(12) United States Patent
Leonard et al.

(10) Patent No.: US 7,524,462 B2
(45) Date of Patent: Apr. 28, 2009

(54) CAPILLARY FLOW FOR A HETEROGENOUS ASSAY IN A MICRO-CHANNEL ENVIRONMENT

(75) Inventors: Leslie Leonard, Portola Valley, CA (US); Klaus Stefan Drese, Mainz (DE); Dirk Boecker, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 592 days.

(21) Appl. No.: 10/113,112

(22) Filed: Mar. 29, 2002

(65) Prior Publication Data

US 2003/0185713 A1   Oct. 2, 2003

(51) Int. Cl.
*G01N 30/00* (2006.01)
*G01N 30/28* (2006.01)

(52) U.S. Cl. .......................... 422/101; 422/56; 422/57; 422/58; 422/59; 422/82; 422/99; 435/286.7; 435/287.6; 435/287.9; 435/288.1

(58) Field of Classification Search ................ 210/656; 422/56–59, 69, 282, 68.1, 82, 99, 101; 435/7.1, 435/286.7, 287.6, 287.9, 288.1; 530/413; 935/108; 436/56, 57
See application file for complete search history.

(56) References Cited

U.S. PATENT DOCUMENTS

| | | |
|---|---|---|
| 4,676,274 A | 6/1987 | Brown |
| 4,857,453 A | 8/1989 | Ullman et al. |
| 5,061,381 A | 10/1991 | Burd |
| 5,137,808 A | 8/1992 | Ullman et al. |
| 5,164,598 A | 11/1992 | Hillman et al. |
| 5,458,852 A | 10/1995 | Buechler |
| 5,589,399 A | 12/1996 | Allen et al. |
| 5,624,850 A | 4/1997 | Kumar et al. |
| 5,693,233 A | 12/1997 | Schembri |

(Continued)

FOREIGN PATENT DOCUMENTS

EP    0 501 796 A2    9/1992

(Continued)

OTHER PUBLICATIONS www.Whatis.com (http://whatis.techtarget.com/definition/0,289893,sid9_gci526632,00.html).*

(Continued)

*Primary Examiner*—Jill Warden
*Assistant Examiner*—Paul S Hyun

(57) ABSTRACT

Apparatus and methods consistent with certain principles related to the present invention include a first channel, where a fluid flows through the first channel, where the first channel comprises an upstream region, a tagging region downstream of the upstream region, where at least one analyte is tagged when the fluid flows through the tagging region, a capture region downstream of the tagging region, where at least one tagged analyte is captured when the fluid flows through the capture region. A second channel communicating the upstream region of the first channel with the first channel intermediate the tagging region and capture regions, where a portion of the fluid flows through the second channel and subsequently flows into the capture region of the first channel, and where the fluid flowing through the tagging region flows into the capture region before the portion of the fluid flowing through the second channel flows into the capture region of the first channel.

10 Claims, 4 Drawing Sheets

U.S. PATENT DOCUMENTS

| | | | |
|---|---|---|---|
| 5,726,404 A | 3/1998 | Brody | |
| 5,750,333 A | 5/1998 | Clark | |
| 5,798,272 A | 8/1998 | Allen et al. | |
| 5,869,004 A * | 2/1999 | Parce et al. | 422/100 |
| 5,916,522 A | 6/1999 | Boyd et al. | |
| 5,919,711 A | 7/1999 | Boyd et al. | |
| 5,922,604 A * | 7/1999 | Stapleton et al. | 436/46 |
| 5,922,615 A | 7/1999 | Nowakowski et al. | |
| 5,976,896 A | 11/1999 | Kumar et al. | |
| 6,001,307 A * | 12/1999 | Naka et al. | 422/81 |
| 6,019,944 A | 2/2000 | Buechler | |
| 6,033,914 A | 3/2000 | Boyd et al. | |
| 6,156,270 A | 12/2000 | Buechler | |
| 6,197,494 B1 | 3/2001 | Oberhardt | |
| 6,228,660 B1 | 5/2001 | May et al. | |
| 6,261,519 B1 * | 7/2001 | Harding et al. | 422/58 |
| 6,296,020 B1 * | 10/2001 | McNeely et al. | 137/806 |
| 6,468,761 B2 * | 10/2002 | Yang et al. | 435/23 |
| 6,479,299 B1 * | 11/2002 | Parce et al. | 436/514 |
| 6,506,609 B1 * | 1/2003 | Wada et al. | 436/148 |
| 2002/0058273 A1 * | 5/2002 | Shipwash | 435/6 |

FOREIGN PATENT DOCUMENTS

| | | |
|---|---|---|
| WO | WO 97/08556 | 3/1997 |
| WO | WO 00/47977 | 8/2000 |

OTHER PUBLICATIONS

Cabrera, C. et al., "Transverse Electrophoresis and Isoelectric Focusing (IEF)," 11 pages, Sep. 6, 2001, www.faculty.washington.edu/yagerp.

Hatch, A., "Diffusion Immunoassay (DIA)," 14 pages, Sep. 7, 2001, www.faculty.washington.edu/yagerp.

/scgukkubg /e,m "Basic Microfluidic Concepts," 8 pages, Sep. 7, 2001, www.faculty.washington.edu/yagerp.

Yager, P., "A New Microfluidic Paradigm for Biological and Biochemical Research," 5 pages, Sep. 7, 2001, www.faculty.washington.edu/yagerp.

* cited by examiner

_US 7,524,462 B2_

CAPILLARY FLOW FOR A HETEROGENOUS ASSAY IN A MICRO-CHANNEL ENVIRONMENT

FIELD OF THE INVENTION

The present invention relates to regulating capillary flow in a microfluidic environment. More particularly, the present invention relates to the control of capillary flow for wash fluids in assays in a microfluidic environment.

BACKGROUND OF THE INVENTION

Microfluidics, the manipulation of microliter volumes in a channel with sub-millimeter dimensions, allow reduction in the required sample volume, a potential decrease in assay completion time and cost reduction for chemical reactions. Microfluidics manipulate fluids by using sequential and parallel analytical processes thus minimizing user manipulation of fluids.

Molecular arrays have been successfully used to perform analytical assays. Such arrays can be used for detection of antibody recognition, analysis of nucleic acid molecules, peptide detection, drug screening, genetic typing and fingerprinting, and disease diagnosis and other analyses known to those skilled in the art of molecular arrays.

An assay in an array can contain binding molecules of several disparate species of a single type or class of molecule (e.g., nucleic acid, or protein), each species being placed on one or more points, or features, on an array. Analytes, such as those found in blood or other body fluid, are usually washed over the entire array in a liquid medium. Analytes bind to specific features in the array because of specific interactions between the analytes and binding molecules contained either in the fluid and/or on the surface of the array. Examples of such specific interactions include, but are not limited to, ligand-receptor interactions, such as antibody-antigen interactions, nucleic acid hybridization, enzyme/substrate, and binding protein-nucleic acid interactions.

Ligand-receptor interactions comprise a number of steps which accomplish functions: (1) combining a test fluid with a specific binding reagent that makes the material of interest detectable (tagging), and (2) selectively retaining the analyte of interest in specific zones by using direct or indirect capture in those zones. These functions can further include: (1) introducing a fluid into a device, (2) tagging any analyte present by reacting the fluid with a specific binding reagent, (3) reacting the fluid containing any tagged analyte with an analyte capturing reagent, (4) removing the analyte of interest from the bulk of un-reacted fluid, (5) washing the region of the device containing the analyte capture reagent, and (6) detecting and analyzing the presence of the analyte in the region containing the analyte capture reagent.

One class of devices for conducting such receptor-ligand assays uses membranous material. In these devices, a membrane is used as a carrier for the specific binding reagent and the analyte capture reagents. Each is localized to specific zones on the membrane and movement of a fluid introduced to the membrane through these zones is accomplished by capillary migration. An example of this type of assay device is a "strip assay."

Another class of devices for conducting ligand-receptor assays is based on "open format" assays. These assays involve the use of tubes, channels, or wells instead of membranes. Specific binding reagents and analyte capture reagents are immobilized on separate zones of the walls of the tubes, channels, or wells, and the reagents react with the fluid as the fluid flows through the zones. In these open format devices, various methods of fluid mechanics, e.g. pumps or gravity, can be used to induce movement of the fluid through the tubes, channels, or wells.

Another method of fluid mechanics used to induce fluid flow utilizes capillary forces in a microfluidic environment. The desire and challenge of combining a simple miniaturized device with processing a small sample volume includes the problem of accomplishing all the desired steps for chemical analysis while avoiding the use of pumps. It is therefore desirable to have a method and system that enables an assay device with channels capable of moving fluids by capillary flow and able to handle volumes necessary for reaction and detection associated with such assays.

SUMMARY OF THE INVENTION

Apparatus and methods consistent with certain principles related to the present invention include a first channel, where a fluid flows through the first channel, where the first channel comprises an upstream region, a tagging region downstream of the upstream region, where at least one analyte is tagged when the fluid flows through the tagging region, a capture region downstream of the tagging region, where at least one tagged analyte is captured when the fluid flows through the capture region. A second channel communicating the upstream region of the first channel with the first channel intermediate the tagging region and capture regions. A portion of the fluid flows through the second channel and subsequently flows into the capture region of the first channel. The fluid flowing through the tagging region flows into the capture region before the portion of the fluid flowing through the second channel flows into the capture region of the first channel.

Additionally, an apparatus and methods consistent with the present invention can include an auxiliary or trigger channel and vents.

Both the foregoing general description and the following detailed description are exemplary and explanatory only and do not restrict the invention, as claimed.

BRIEF DESCRIPTION OF THE DRAWINGS

The accompanying drawings, which are incorporated and constitute a part of this specification, illustrate several embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Whenever possible, the same reference numbers will be used throughout the drawings to refer to the same or like parts. It is noted that, as used in this specification and the appended claims, the singular form "a," "an," and "the" include plural referents unless expressly and unequivocally limited to one referent. Thus for example, reference to "an analyte" includes two or more analytes.

For the purposes of this specification and appended claims, unless otherwise indicated, all numbers expressing size, proportions, dimensions, quantities, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Figure 1:
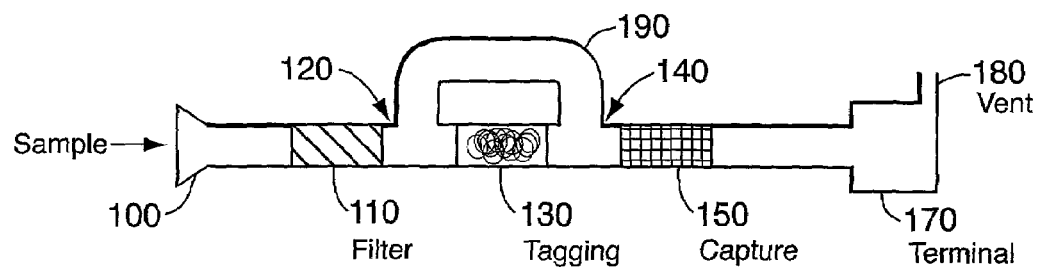
FIG. 1 illustrates a receptor-ligand assay device comprising four regions and a second channel connected to the first channel that diverts a portion of the fluid for use in the washing step.

FIG. 1 shows a receptor-ligand assay device comprising first channel 100 and second channel 190. First channel 100 comprises four regions. In one non-limiting embodiment, filter region 110 contains a filter. A filter can contain materials capable of removing particles or compounds from the fluid. The materials capable of removing particles or compounds include absorbent paper filter or glass fiber or nylon membranes. Commercial sources of these materials are well known in the art, e.g., Whatman filters or HemaSep® or CytoSep® filters from the Pall Corporation of East Hills, N.Y.

In one non-limiting embodiment, downstream of filter region 110 in FIG. 1 is tagging region 130 where the fluid flowing through first channel 100 can be combined with an analyte recognition molecule or tagging reagent. The function of the analyte tagging reagent is to bind or interact with the analytes in such a way that a signal representing the presence of that analyte can be detected in capture region 150. For any ligand-receptor interaction, like antibody-antigen, nucleic acid base pairing, DNA-protein, etc., one interaction or one member is either labeled directly or indirectly. Tagging reagents can include radioactive or optical tags for colorimetric, luminescent, fluorescent, chemiluminescent, or electrochemiluminescent detection and other means for detection known to one skilled in the art of chemical analysis.

In one non-limiting embodiment, analyte capture region 150 follows tagging region 130. In capture region 150, the tagged fluid contacts one or more immobilized analyte capture reagents. The capture reagent can be any compound to which the desired analyte can bind, including, for example, nucleic acid sequences, proteins, enzymes, enzyme substrates, antibodies, or antigens for antibodies.

In one non-limiting embodiment, terminal 170 can be located at the end of first channel 100 to collect the fluid and washing reagent after flowing downstream through first channel 100. Terminal region 170 can comprise a larger, empty microfluidic channel, or a channel containing an absorbent material capable of absorbing and retaining the fluid and washing reagent. The ability of the material to absorb fluid can depend on the amount of drawing force desired for assisting flow through first channel 100. The material can be a filter such as paper or an absorptive material, such as a sponge or absorptive chemical. Examples of such materials include absorbent paper filter, glass fiber or nylon membranes, sodium polyacrylate, hygroscopic materials, and other absorbent materials known to one skilled in the art of chemical terminal disposal. In another non-limiting embodiment, terminal region 170 further includes vent 180, used as a means for releasing any gas or inert substance in the channel.

Second channel 190 communicates with first channel 100 at bifurcation area 120. Bifurcation area 120 is upstream of tagging region 130. The upstream region is further described with respect to FIG. 9. Second channel 190 reconnects with first channel 100 in reconnection region 140, which is downstream of tagging region 130. Second channel 190 can be used to reintroduce a portion of the fluid flowing in first channel 100 as a wash reagent. A portion of the fluid flowing through first channel 100 flows into second channel 190 and returns to first channel 100 before entering capture region 150. Second channel 190 can have various structures or designs for enhancing or retarding flow through this channel.

In one non-limiting embodiment, the fluid in second channel 190 reenters first channel 100 after most of the fluid in first channel 100 has passed the reconnection region 140. In order to maintain fluid connectivity, a portion of the fluid in second channel 190 should contact a portion of the fluid in first channel 100.

Figure 2A:
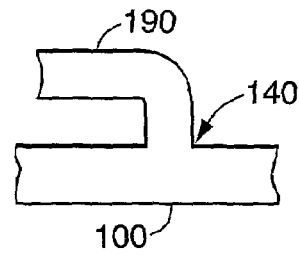
FIGS. 2A-2C illustrate the movement of fluid in the reconnection region of a receptor-ligand assay device.
Figure 2B:
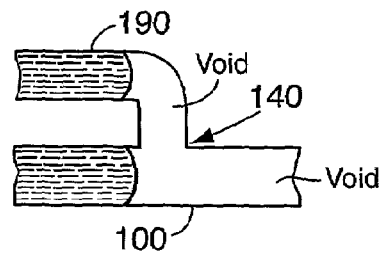
Figure 2C:
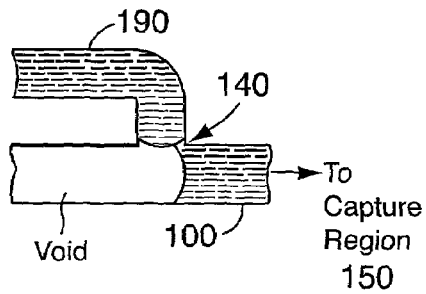

FIGS. 2A-2C illustrate the flow in first channel 100 and second channel 190 necessary to achieve fluid connectivity. FIG. 2A illustrates empty first channel 100 and second channel 190 at the reconnection region 140. FIG. 2B illustrates fluid flowing in first channel 100 and second channel 190, prior to reaching reconnection region 140. FIG. 2C illustrates the positions of the flow in first channel 100 and second channel 190 as they connect. The fluid flow in first channel 100 passes through the reconnection region 140 and, as it is passing through the reconnection region, the fluid flow in second channel 190 begins to enter reconnection region 140 and the first channel 100. The size, shape, and length of second channel 190 vary depending on how much fluid is desired to be kept for a washing step, as well as to control the time it takes the fluid to rejoin first channel 100. The dimensions of a microfluidic channel can vary depending upon the application. In one non-limiting embodiment, for a body fluid, e.g., blood, analysis device, the channel can have diameter ranging from 50-500 microns. In another non-limiting embodiment, the channel can have a diameter ranging from 75-200 microns. The length of any given section of microchannel is varied for the analyte processing to be done within that section. These sections may range in length from 100 microns to 50 millimeters, more preferably in the range of 500 microns to 20 millimeters. Microfluidic devices are made by a wide variety of methods known to those skilled in the art, including molding polymeric materials, etching silicon substrates, or assembling multi-laminate structures using polymers such as polyamide.

Figure 3:
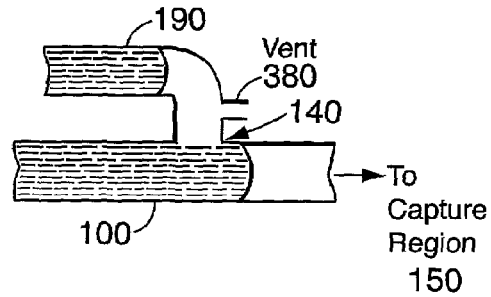
FIG. 3 illustrates the movement of fluid in the reconnection region of a receptor-ligand assay device where the second channel includes a vent.

FIG. 3 illustrates the addition of vent 380 to second channel 190 before reconnection region 140. In one non-limiting embodiment, vent 380 provides a means for the escape of gas trapped in the channels so that the fluid can move forward. The gas that fills the channels can be air or an inert gas. As the fluid enters second channel 190, it displaces the gas in second channel 190 and forces the gas to move toward the reconnection region 140 of first channel 100. If the fluid in the second channel 190 is moving slower than the fluid in the first channel 100, then the gas pressure in the second channel 190 increases. As illustrated in FIG. 3, the fluid in first channel 100 has moved past the reconnection region 140, while the fluid in second channel 190 has not yet reached the reconnection region 140. Gas builds up in the area between the fluids where vent 380 can be located. Vent 380 gives second channel 190 a means for releasing the gas and thus allowing the fluid to continue to fill second channel 190 and reconnect with first channel 100. Vent 380 can, thus, control the timing of the reconnection of the fluid from second channel 190 with first channel 100. The control can be achieved through the use of pressure on a valve or vent 380. Vent 380 can be made hydrophobic by plasma treatment, or by coating with biomolecules, to prevent fluid from flowing into vent 380.

Figure 4A:
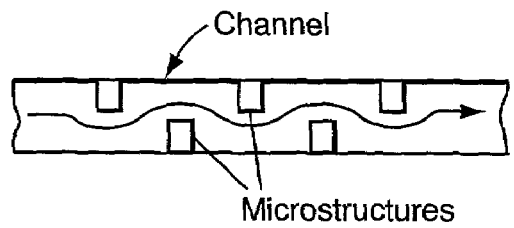
FIGS. 4A and 4B illustrate methods of controlling flow rates in a receptor-ligand assay device.
Figure 4B:
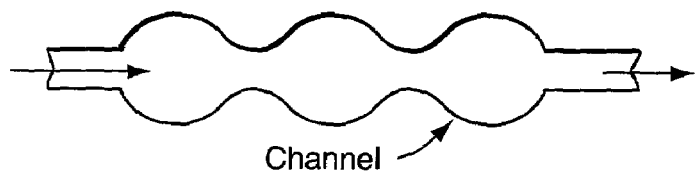

In one non-limiting embodiment second channel 190 can incorporate additional means to reduce flow rate. FIGS. 4A and 4B illustrate means of controlling flow rate by changing features of a channel. FIG. 4A illustrates adding microstructures to a channel to reduce flow rate. Through the use of specific capillary structures and geometry, flow is restricted in regions of high capillary resistance in ways known in the art of microfluidics.

In another non-limiting embodiment, channels can be made of a different, relatively more hydrophobic material, for example naturally hydrophobic materials such as, plastics, elastomers, polystyrene, polypropylene, silicon-based elatomers, or can be coated to make the interior walls hydrophobic, e.g. coating with fatty acids. Other methods of controlling flow include making surfaces hydrophilic by plasma treatment, or by coating with biomolecules, thus causing flow to increase.

Figure 5A:
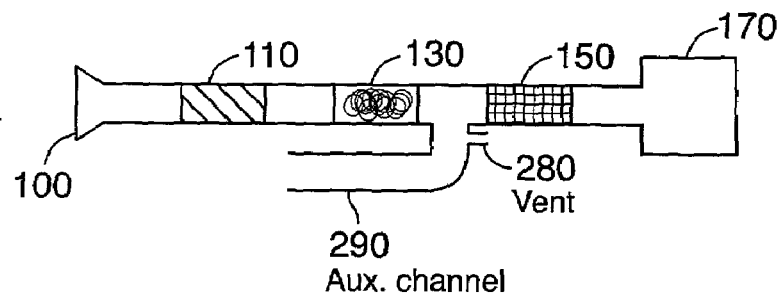
FIGS. 5A and 5B illustrate receptor-ligand assay devices comprising four regions and an auxiliary channel connected to the first channel that can introduce washing reagent into the first channel during the washing step.
Figure 5B:
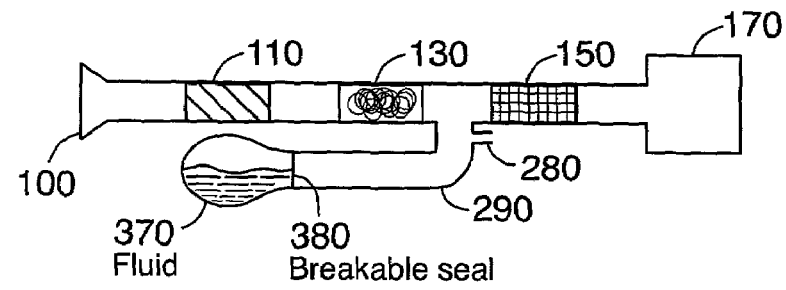

FIGS. 5A and 5B illustrate non-limiting embodiments of a direct capture, receptor-ligand assay device comprising first channel 100 with four regions and auxiliary channel 290 connected to the first channel. Auxiliary channel 290 provides a means for introducing a fluid such as a washing reagent or a reference/calibration reagent into first channel 100 before capture region 150. The washing reagent follows the fluid through first channel 100.

In one embodiment, the reagent washes away non-specific material, including excess or unbound tagging reagent that can cause interference in measurement of the analytes tagged in the tagging region that create a detectable signal in capture region 150.

FIGS. 5A and 5B illustrate embodiments, in which a fluid (e.g., fluid 370 of FIG. 5B) is introduced into auxiliary channel 290 at one end of auxiliary channel 290 and flows into first channel 200. The size and shape of auxiliary channel 290 can vary according to the volume of reagent being introduced, and the flow rate desired for the wash reagent. In one embodiment, the wash reagent can be controlled such that it enters first channel 100 after most of the fluid has passed the junction where auxiliary channel 290 joins first channel 100. At the same time, the flow should be controlled to allow fluidic connectivity to be maintained. Means for controlling the flow include timing the introduction of fluid into auxiliary channel 290, varying the size and shape of the channel, incorporating microstructures into the channel, or causing chemical modification of materials. Through the use of specific capillary structures, like those illustrated in FIGS. 4A and 4B, flow is restricted in regions of high capillary resistance in ways known in the art of microfluidics. In alternate embodiments, auxiliary channel 290 can be made of a different, relatively more hydrophobic material than the first channel 100, such as naturally hydrophobic materials such as, plastics, elastomers, polystyrene, polypropylene, silicon-based elatomers, or can be coated to make them hydrophobic, e.g. coating with fatty acids. Other methods of manipulating flow include surfaces made more hydrophilic by plasma treatment, or by coating with biomolecules. Vent 280 can also be incorporated into auxiliary channel 290 before the junction where auxiliary channel 290 joins first channel 100, with similar effects and benefits of vent 380 of FIG. 3.

Figure 6A:
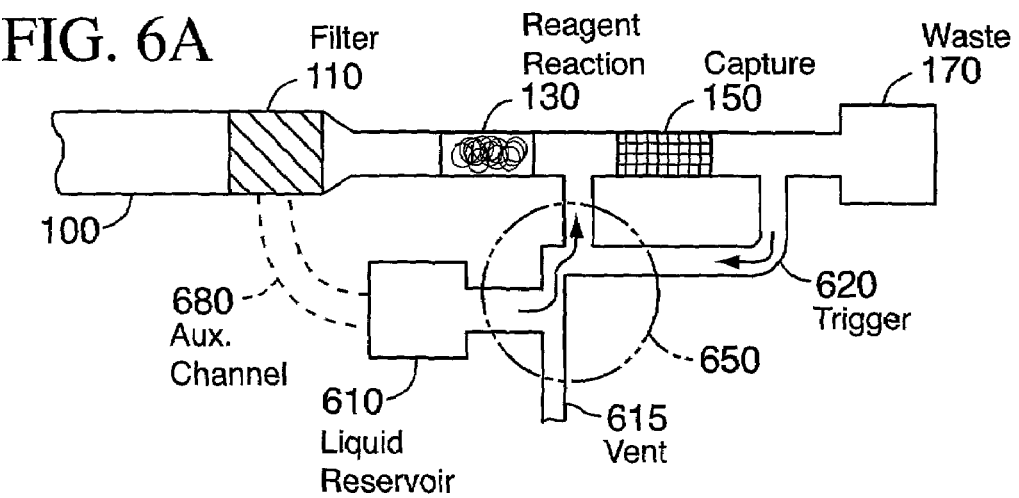
FIGS. 6A-6B illustrate a trigger mechanism for controlling the flow of fluid from an auxiliary channel into a first channel.
Figure 6B:
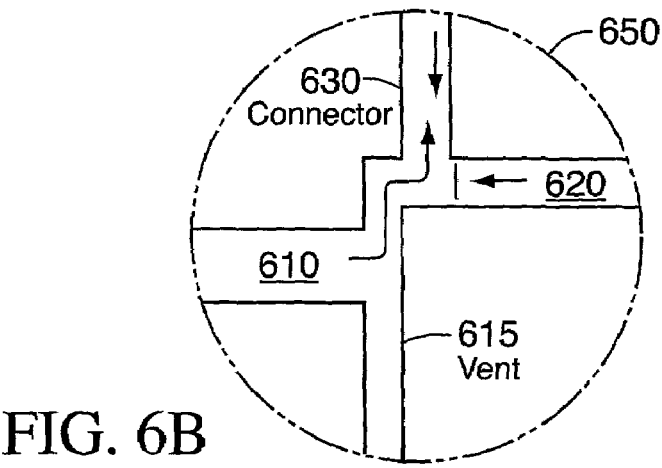

FIGS. 6A-6B illustrate one non-limiting embodiment in which a fluid is introduced into first channel 100 from liquid reservoir 610 through the use of trigger channel 620 and vent 615. FIG. 6A illustrates one non-limiting embodiment of a structure utilizing a trigger mechanism for controlling the flow of fluid from an auxiliary or second channel into a first channel. In one embodiment liquid reservoir 610 can be filled using material from first channel 100. In another embodiment, liquid reservoir 610 can be filled by the user with a pre-filled fluid through the use of an auxiliary source of liquid, within the device or introduced by the user. In one embodiment, trigger channel 620 can be connected to first channel 100 before terminal region 170. In an alternate embodiment, trigger channel 620 can be connected to first channel 100 in other locations. In another embodiment, trigger channel 620 can not be connected to first channel 100, but can be connected to an outside source of liquid. Trigger channel 620, through the use of specific capillary structures and geometry, like those described in FIG. 4, can control flow timing in ways known in the art of microfluidics. The diameter of vent 615 is small compared to the main channels to allow for gas escape and to prevent fluid backflow.

In one embodiment, all of the channels described in FIG. 6A begin unfilled. The fluid enters first channel 100. The fluid flows through filter 110 and continues to flow downstream through first channel 100. In one embodiment, some of the fluid can flow into liquid reservoir 610 through auxiliary channel 680, filling liquid reservoir 610. The fluid in liquid reservoir 610 does not continue into first channel 100, due to the lack of fluidic connectivity. Fluid in first channel 100 flows downstream through tagging region 130, capture region 150, and toward terminal region 170.

FIG. 6B describes elbow area 650, which controls the flow of fluid from liquid reservoir 610 to first channel 100. Fluid flows from first channel 100 down connection channel 630 and fills connection channel 630. After fluid flows through capture region 150, a portion enters trigger channel 620. Fluid then backflows through trigger channel 620 toward connection channel 630. The fluid in trigger channel 620 eventually creates a fluidic connection between liquid reservoir 610 and connection channel 630, thus "triggering" fluid flow from liquid reservoir 610 through connection channel 630 to first channel 100. Fluid from liquid reservoir 610 then flows through capture region 150 and into terminal region 170.

Figure 7:
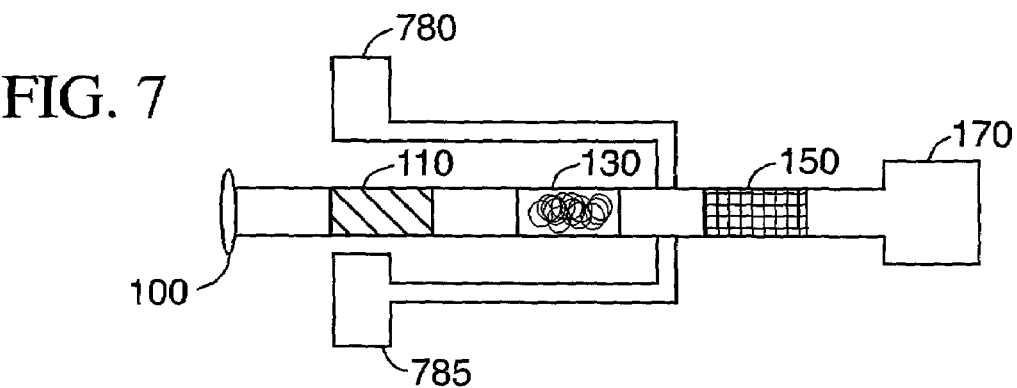
FIG. 7 illustrates a receptor-ligand assay device comprising four regions and two auxiliary channels connected to the first channel, both capable of introducing washing reagent to the first channel.

FIG. 7 illustrates an alternative embodiment for the receptor-ligand assay device. In the device illustrated by FIG. 7, there are two separate auxiliary channels 780 and 785, each capable of introducing fluid into first channel 100 before capture region 150. Auxiliary channel 780 and 785 can contain different fluids, which can be introduced into the first channel in succession or in combination.

Figure 8:
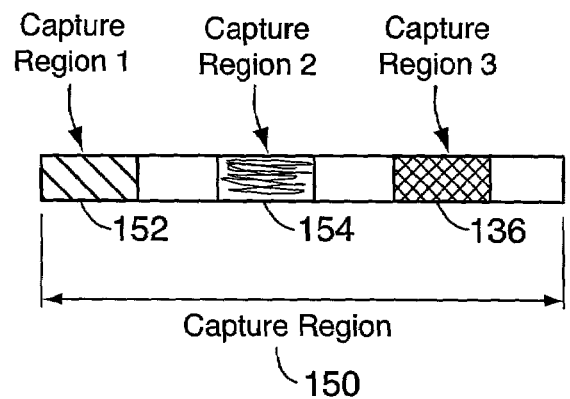
FIG. 8 illustrates an analyte capture region within a receptor-ligand assay device comprising multiple sub-capture regions in series.

FIG. 8 illustrates an alternative embodiment for capture region 150 described previously. Capture region 150 comprises multiple sub-capture regions 152, 154, and 156 in series, each capable of selectively binding different analytes. These sub-capture regions can have different sizes, depending on the needs of the assay, and can be spaced apart from each other or follow immediately after one another.

Figure 9:
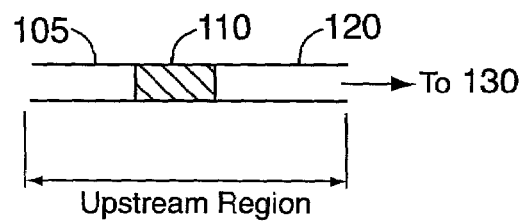
FIG. 9 illustrates an upstream region within a receptor-ligand assay device.

FIG. 9 illustrates the upstream region. The upstream region is located upstream of tagging region 130. This upstream region includes region 105 before filter region 110 and bifurcation region 120.

Figure 10:
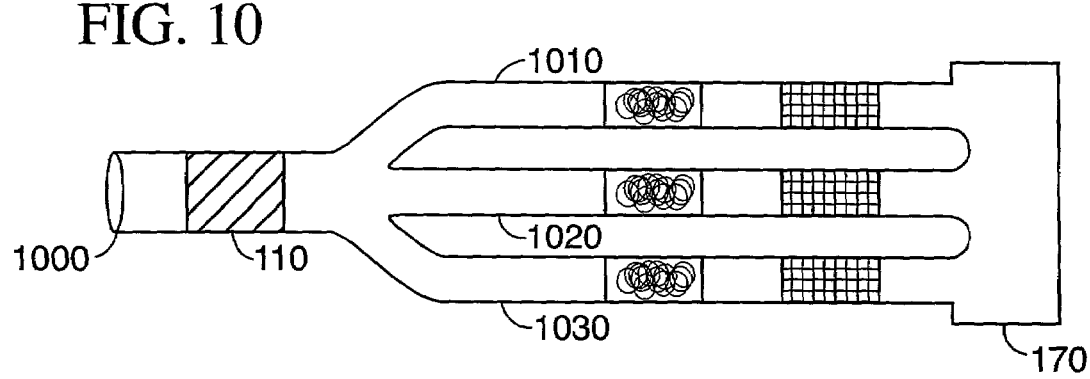
FIG. 10 illustrates a receptor-ligand assay device comprising multiple channels in parallel.

FIG. 10 illustrates an alternative embodiment for the assay device described previously. This embodiment combines multiple parallel channels 1010, 1020, and 1030 in one assay device. Parallel channels 1010, 1020, and 1030 can be capable of detecting one or more analytes. In one embodiment (not shown), each channel can include its own individual second channel or auxiliary channel, or share auxiliary channels. One filter region 110 can be placed before the fluid is divided between the multiple channels. Alternatively, each channel can contain its own filter region (not shown). One terminal region 170 is provided at the terminal end of the channels. Alternatively, each channel can contain its own terminal region (not shown).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus comprising:
   a first channel, wherein a fluid introduced to the apparatus flows through said first channel, wherein said first channel comprises:
      an upstream region;
      a tagging region downstream of said upstream region, wherein an analyte is tagged when said fluid flows through said tagging region by interacting with a tagging reagent present in the tagging region;
      a capture region downstream of said tagging region, wherein at least one tagged analyte is captured when said fluid flows through said capture region by binding to at least one analyte capture reagent immobilized in the capture region;
   a second channel communicating said upstream region of said first channel with said first channel intermediate said tagging region and capture region, wherein a portion of said fluid flows through said second channel and subsequently flows into said capture region of said first channel; and
   wherein said second channel comprises means for retarding flow rate, whereby fluid flowing through said tagging region flows into said capture region before said portion of said fluid flowing through said second channel flows into said capture region of said first channel.

2. The apparatus according to claim 1, wherein said first channel and said second channel are adapted for capillary flow of said fluid.

3. The apparatus according to claim 1, wherein said upstream region further comprises:
   a filter region, comprising a filter.

4. The apparatus according to claim 1, wherein said first channel further comprises:
   a terminal region, downstream of said capture region, said terminal region adapted to absorbing said fluid.

5. The apparatus according to claim 1, further comprising a vent communicating with the second channel.

6. An apparatus comprising:
   a first channel, wherein a first fluid introduced to the apparatus flows through said first channel, wherein said first channel comprises:
      an upstream region;
      a tagging region downstream of said upstream region, wherein an analyte is tagged when said first fluid flows through said tagging region by interacting with a tagging reagent present in the tagging region;
      a capture region downstream of said tagging region, wherein at least one tagged analyte is captured when said first fluid flows through said capture region by binding to at least one analyte capture reagent immobilized in the capture region;
   a second channel in fluid communication with said first channel intermediate said tagging region and said capture region;
   a trigger channel communicating with said first channel, wherein said first fluid flows through said trigger channel toward said second channel, causing a second fluid to flow through said second channel and subsequently flow into said capture region of said first channel;
   wherein said second channel comprises means for retarding flow rate, whereby first fluid flowing through said tagging region flows into said capture region before said second fluid flows through said second channel into said capture region of said first channel.

7. The apparatus according to claim 6, wherein said first channel and said second channel are adapted for capillary flow of said fluid.

8. The apparatus according to claim 6, wherein said upstream region further comprises:
   a filter region, comprising a filter.

9. The apparatus according to claim 6, wherein said first channel further comprises:
   a terminal region, downstream of said capture region, said terminal region adapted to absorbing said fluid.

10. The apparatus according to claim 6, wherein said second channel contains a vent.

\* \* \* \* \*